United States Patent [19]

Shimada et al.

[11] Patent Number: 5,462,691
[45] Date of Patent: Oct. 31, 1995

[54] SKIN CLEANSING AGENT

[75] Inventors: Tadahiro Shimada, Yokosukashi; Sachiko Yuki, Ebina; Tomoko Iizuka, Tokyo, all of Japan

[73] Assignee: Shiseido Co., Ltd., Tokyo, Japan

[21] Appl. No.: 128,132

[22] Filed: Sep. 29, 1993

[30] Foreign Application Priority Data

Sep. 29, 1992 [JP] Japan .................................. 4-282238

[51] Int. Cl.$^6$ ........................................................ C11D 7/26
[52] U.S. Cl. ............................ 252/174.15; 252/174.21; 252/174.22
[58] Field of Search ........................ 252/174.15, 174.21, 252/174.22

[56] References Cited

U.S. PATENT DOCUMENTS

| | | | |
|---|---|---|---|
| 3,795,624 | 3/1974 | Feinstone . | |
| 5,063,044 | 11/1991 | Kohl et al. | 252/174.15 X |
| 5,100,655 | 3/1992 | Takano et al. | 252/174.15 X |
| 5,198,210 | 3/1993 | Critchley et al. | 252/174.15 X |
| 5,206,020 | 4/1993 | Critchley et al. | 252/174.15 X |

FOREIGN PATENT DOCUMENTS

| | | |
|---|---|---|
| 0463496 | 6/1991 | European Pat. Off. . |
| 63-122618 | 5/1988 | Japan . |

*Primary Examiner*—Paul F. Shaver
*Attorney, Agent, or Firm*—Townsend & Banta

[57] ABSTRACT

The present invention provides a skin cleansing agent which is capable of performing, in a one-stage process, both make-up removal and bare skin cleansing to clear off dirt and sebum on the skin. In particular, a non-oil skin cleansing agent is provided that is characterized by containing 1.0–80 wt % of polyethylene glycol diisostearate and/or polyethylene glycol dioleate with an added mole number of ethylene oxide of 10–18.

13 Claims, No Drawings

SKIN CLEANSING AGENT

BACKGROUND OF THE INVENTION

1. Field of the Invention

This invention relates to new skin cleansing agents and more specifically to skin cleansing agents which can remove make-up such as lipstick, foundation, mascara, eye shadow, etc., as well as wash bare skin to clean off dirt and sebum from the skin in a one stage process.

2. Description of Related Art

Conventionally, people who wear oil-containing make-up such as lipstick, foundation, mascara, eye shadow, etc., would, when washing their faces, first use a face washing agent(s) for make-up removal, which contains a lot of solvent oil(s) which mixes well with make-up, such as cleansing cream, cleansing oil, cleansing milk or cleansing gel, and then secondly wash off the residual oil(s) of the cleansing agent(s) (cleansing cream, cleansing oil, cleansing gel, cleansing milk, etc.) as well as sebum and dirt from the skin by using a face washing agent(s) for bare skin cleansing, such as a strongly water soluble soap or cleansing foam, thus achieving the satisfaction of feeling clean and refreshed.

The reason why such two-stage cleansing is needed is that: rinsing with water or warm water immediately after using creams and such, for make-up removal which contains a lot of oil(s), does not sufficiently remove residual oil(s) from the skin and the refreshing cleansed feeling cannot be obtained. Whereas cleansing by using only cleansing agents, such as soap does not sufficiently remove the pigments, coloring materials and such, which are covered with oil(s) on the skin.

However, a fast and simple make-up removal procedure has recently been increasingly in demand and thus products that can answer this demand are sought after in the market. Therefore, skin cleansing agents which have both a make-up removal effect and a bare skin cleansing effect, i.e. give a clean and refreshed feeling, with only a one-stage process are desired. Such a one-stage skin cleansing agent, for example, is disclosed in Japanese patent publication (Tokkai) Sho-63-122618.

However, for sweat resistant and water resistant lipsticks, foundation, mascara, eye shadow, etc., having a long-lasting make-up effect which have been developed recently, i.e. the so-called "hard make-up ", the one-stage skin cleansing agents which have been reported thus far have not been satisfactory in terms of the cleansing effect and feel during use.

SUMMARY

It is the object of the present invention to provide a skin cleansing agent which is capable of performing, in a one-stage process, both make-up removal and bare skin cleansing to clear off dirt and sebum from the skin.

DETAILED DESCRIPTION OF THE INVENTION

For sweat resistant and water resistant lipsticks, foundation, mascara, eye shadow, etc., with a long-lasting make-up effect which have been developed recently, i.e. the so-called "hard make-up", the one-stage skin cleansing agents which have been reported thus far were not satisfactory in terms of the cleansing effect and feel during use. The present invention provides a skin cleansing agent which is capable of performing, in a one-stage process, both make-up removal and bare skin cleansing to clear off dirt and sebum on the skin.

The inventors have worked earnestly to solve the problem of a one-stage process of both make-up removal and bare skin cleansing and as a result, found out that surfactants of specific types and structures showed excellent effects.

A non-oil skin cleansing agent characterized by containing 1.0–80 wt % of polyethylene glycol diisostearate and/or polyethylene glycol dioleate with an added mole number of ethylene oxide of 10–18 is provided.

The skin cleansing agent(s) of this invention has an effect of cleansing off the oil(s) of make-up and such, and also it can be rinsed off with water to give a clean and refreshing bare skin cleansing effect. The appearance of this cleansing agent may be clear or cloudy whim. Polyethylene glycol dioleate and polyethylene glycol diisostearate used in the skin cleansing agent of this invention are ideal as one-stage cleansing surfactants because: they are in a liquid form at room temperature and are excellent in formulation stability, and not only mix well with oil make-up but, in the water rinsing process, self-emulsify and rinse off well so that it is easy to rinse off dirt and make-up from the skin, giving a clean and refreshed feeling after use.

The added mole number of ethylene oxide is preferably 10–18, and more preferably 11–13. When the added mole number of ethylene oxide is less than 10, lipophilicity is strong and sufficient mixing with oil make-up is achieved, but water rinsing is insufficient and the bare skin cleansing effect is weak. Stability over time is not good either. When the added mole number of ethylene oxide is more than 18, mixing with oil make-up is not sufficient and that which is meant to be cleansed off remains on the skin, rendering the make-up removal effect insufficient.

When blending, the compounds mentioned above are used individually or in combination. The amount to be blended is preferably 1.0–80 wt % of the total amount of the cleansing agent, and more preferably 6–20 wt %. If the amount is less than 1.0 wt %, then the cleansing power is not sufficient, whereas even if the amount is more than 80 wt %, the effect does not improve any further and there is a cost disadvantage as well as being undesirable from a safety standpoint.

The skin cleansing agent of this invention may contain an additional 30 wt % or less of polyethylene glycol monoisostearate and/or polyethylene glycol monooleate with an added mole number of ethylene oxide of 4–14. The addition of these polyethylene glycol mono-fatty acid esters generally reinforces the bare skin cleansing effect. When the added mole number of ethylene oxide is less than 4, lipophilicity is strong and sufficient mixing with oil make-up is achieved, but water rinsing is insufficient and the bare skin cleansing effect is weak. When the added mole number of ethylene oxide is more than 14, mixing with oil make-up is not sufficient and that which is meant to be cleansed off remains on the skin, rendering the make-up removal effect insufficient.

The amount to be blended is up to 30 wt % of the total amount of the cleansing agent. If it is more than 30 wt %, then the entire system becomes hydrophilic and the make-up removal effect decreases, and also it is not desirable from a safety standpoint.

Another surfactant which can be used in this invention is polyoxyalkylene modified polysiloxane. This is a prior-art material, and compatible with other ingredients in the base system. In particular, it easily emulsifies hard make-up containing silicone oils and silicone modified powder so that they can be wiped off with water rinsing. The structural formula is shown below.

Chemical Formula:

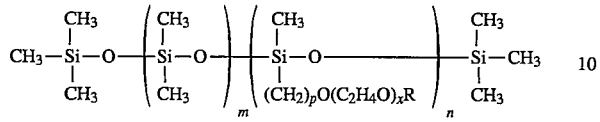

In the formula, R is a hydrogen or an alkyl group with a carbon number of 1–5, p is an integer in the range of 1–5, x is an integer in the range of 5–30, and m and n are integers in the range of 1–15.

A typical example would be a co-polymer of dimethyl siloxane and methyl (polyoxyethylene) siloxane with the added amount of the ethylene oxide of 5–500 moles. They can be used individually or in combinations of two or more types. The amount to be blended is preferably 0.5–30 wt % of the total amount of the skin cleansing agent, and more preferably 3–20 wt %. If the amount is more than 30 wt %, then it is not desirable from the skin safety standpoint and also disadvantageous in terms of cost.

Additionally, one or more items from among lower alcohols and polyatomic alcohols as well as compounds made by adding ethylene glycol or propylene oxide to them, may be blended to the skin cleansing agent of this invention.

The water soluble compounds with hydroxyl groups as described above which may be used in this invention are, for example: ethyl alcohol, isopropyl alcohol, butanol, propylene glycol, isopropyl glycol, 1, 3 butanediol, dipropylene glycol, glycerine, diglycerine, polyglycerine, trimethylolpropane, erythritol, pentaerythritol, sorbitan, sorbitol glucose, mannitol, saccharose, trehalose and fructose, as well as their derivatives made by adding ethylene oxide, propylene oxide, etc. to them. Particularly preferable are ethanol, dipropylene glycol, 1, 3 butanediol, etc. These are used individually or in combinations of two or more types. Of these, those which are rather hydrophobic such as dipropylene glycol have a superior cleansing effect against hard make-up and thus are desirable for the cleansing agent of this invention.

The amount of these water soluble compounds with hydroxyl groups to be blended is preferably 1–40 wt % of the total amount of the cleansing agent of this invention. More preferable is 5–20 wt %. The balance of all the ingredients is water to comprise the total of 100.00 wt %.

The skin cleansing agent of this invention is preferably substantially without oil. However, if oil is contained, then the clear and refreshed feeling from the bare skin cleansing effect may become unsatisfactory. The make-up removal effect can be sufficiently achieved without oil. The oil mentioned here which may be used, may be, for example: hydrocarbons, higher alcohols, higher fatty acids, higher fatty acid esters of higher alcohols, animal or vegetable fat or oil, fatty acid esters of cholesterol, and silicones. Concrete examples are liquid paraffin, polyisobutene, isostearyl cholesteryl ester, triglyceride 2-ethylhexanoate, hexadecyl 2-ethylhexanoate, octadecyl myristate, olive oil, chain or cyclic methylpolysiloxane, etc.

The skin cleansing agent of this invention uses the ingredients mentioned above in a liquid form, or a water soluble thickener is added to obtain a viscous or jelly form for use.

In these cases, the composition can be determined by blending tests of the ingredients which are normally conducted by specialists in this field. The skin cleansing agent of this invention can be manufactured by normally employed processes.

Cosmetics, items commonly used in medical products such as thickeners, ionic surfactants, active agents, moisture retainers, anti-inflammatories, disinfectants, preservatives, ultraviolet absorbents, anti-oxidants, organic and inorganic powder, pigments, perfumes, etc., can be additionally added to the skin cleansing agent of this invention as necessary.

The skin cleansing agent of this invention is mainly used as a face washing agent to remove make-up, but it can also be used for cleansing or massage.

This invention is explained here by referring to examples. This invention is not limited to these examples.

EXAMPLES

EXAMPLES 1–7 AND COMPARATIVE EXAMPLES 1–9

The skin cleansing agents of examples 1–7 and comparative examples 1–9, with the compositions (wt %) listed in Tables 1 and 2 (respectively) were prepared according to the procedure described below, and their feel during use was evaluated based on the evaluation criteria described below. The results are shown in the Tables 1 and 2.

Preparation

The water soluble thickener(s) which was not easy to dissolve in water was dissolved beforehand and added to the main pot along with the other ingredients, and homogeneous mixing was conducted by a high speed mixer. After defoaming and filtering, the skin cleansing agent was obtained.

Ingredient A *1) has the following composition:

| | |
|---|---|
| Polyethylene glycol 1500 | 2 (wt %) |
| Glycerine | 3 |
| 1,3 butylene glycol | 5 |
| Xanthan gum | 0.5 |
| Methyl cellulose | 2 |
| Sodium alginate | 0.5 |
| POE (12) POP (6) butyl alcohol ether | 5 |

Evaluation method and evaluation criteria
(A) Removal of foundation and feel during use Eighteen healthy and normal women (age 20–45) rinsed their bare skin with water, dried the skin and then applied a water resistant oil foundation (perspiration resistant and water resistant foundation) on their faces. 30 minutes later, agents of this invention and comparative agents were mixed into the oil foundation, and after water rinsing, the removal of the foundation (make-up removal effect) and the refreshed feeling after use (bare skin cleansing effect) were evaluated. Each evaluation was conducted with the highest evaluation grade being 100, and the average of the grades from 18 women was used.
1) Make-up removal effect
Star circle: Evaluation grade of 75 or higher (very good removal)
Single circle: Evaluation grade of 50–75 (fair removal)
Triangle: Evaluation grade of 25–50 (hard to remove make-up)
X: Evaluation grade of 25 or lower (make-up was not removed)

2) Bare skin cleansing effect

Star circle: Evaluation grade of 75 or higher (very refreshing)
Single circle: Evaluation grade of 50–75 (refreshing)
Triangle: Evaluation grade of 25–50 (residue is felt)
X: Evaluation grade of 25 or lower (significant residue is felt)

(B) Stability over time

After preparation, glass bottles (with lids) were filled to 90% full with the agents of the invention and the comparative agents, and let stand in a thermostatic bath at 45° C. The states of the agents were observed over time, and the evaluation was conducted based on the evaluation criteria described below after 4 weeks.

Star circle: After 4 weeks under the temperature condition of 45° C. or higher, the gel state was stable.
Single circle: The viscosity of the gel somewhat decreased.
Triangle: The gel was softened (semi-separated)
X: Separated.

TABLE I

|  | Examples |  |  |  |  |  |  |
|---|---|---|---|---|---|---|---|
|  | 1 | 2 | 3 | 4 | 5 | 6 | 7 |
| Ingredient A *1) | 18 | 18 | 18 | 18 | 18 | 18 | 18 |
| PEG400 dioleate | — | 5 | 5 | 5 | — | — | — |
| PEG400 monoisostearate | — | 5 | 5 | 5 | — | — | — |
| PEG450 diisostearate | — | — | — | — | — | 30 | — |
| PEG600 diisostearate | 20 | 5 | 5 | 5 | 30 | — | — |
| PEG750 diisostearate | — | — | — | — | — | — | 30 |
| PEG800 dioleate | — | 5 | 5 | 5 | — | — | — |
| POE (20) glycerine monooleate | — | — | — | — | — | — | — |
| Dimethyl siloxane methyl (polyoxyethylene 60) siloxane copolymer | 10 | 10 | 10 | 10 | — | — | — |
| POE (20). POP (8) octyldodecylether | — | — | — | — | — | — | — |
| Sodium methyl cocoyl taurate | — | — | 1 | — | — | — | — |
| Alkyl imidazoline | — | — | — | 3 | — | — | — |
| Isopropyl myristate | — | — | — | — | — | — | — |
| EDTA-3Na.2H$_2$O |  |  |  |  |  |  |  |
| Methyl parabane | 0.05 | 0.05 | 0.05 | 0.05 | 0.05 | 0.05 | 0.05 |
| Perfume | 0.1 | 0.1 | 0.1 | 0.1 | 0.1 | 0.1 | 0.1 |
| Purified water | 0.05* | 0.05* | 0.05* | 0.05* | 0.05* | 0.05* | 0.05* |
| Stability over time | ✪ | ○ | ○ | ○ | ✪ | ✪ | ✪ |
| Panel test results |  |  |  |  |  |  |  |
| Make-up removal effect | ✪ | ✪ | ✪ | ✪ | ✪ | ✪ | ○ |
| Bare skin cleansing effect | ✪ | ✪ | ✪ | ✪ | ✪ | ○ | ✪ |

*Balance to 100 wt %

TABLE II

|  | Comparative Examples |  |  |  |  |  |  |  |  |
|---|---|---|---|---|---|---|---|---|---|
|  | 1 | 2 | 3 | 4 | 5 | 6 | 7 | 8 | 9 |
| Ingredient A *1) | 18 | 18 | 18 | 18 | 18 | 18 | 18 | 18 | 18 |
| PEG400 dioleate | 20 | — | — | — | — | — | — | — | — |
| PEG400 monoisostearate | — | — | — | — | — | — | — | — | — |
| PEG450 diisostearate | — | — | — | — | — | — | — | — | — |
| PEG600 diisostearate | — | — | — | — | — | — | — | — | 5 |
| PEG750 diisostearate | — | — | — | — | — | — | — | — | — |
| PEG800 dioleate | — | — | — | 20 | — | — | — | — | — |
| POE (20) glycerine monooleate- | — | — | 20 | — | — | — | — | — | 15 |

TABLE II-continued

|  | Comparative Examples | | | | | | | | |
|---|---|---|---|---|---|---|---|---|---|
|  | 1 | 2 | 3 | 4 | 5 | 6 | 7 | 8 | 9 |
| Dimethyl siloxane methyl (polyoxyethylene 60) siloxane copolymer | 10 | 10 | 10 | 10 | 30 | — | — | — | 10 |
| POE (20). POP (8) octyldodecylether | — | — | — | — | — | 30 | — | — | — |
| Sodium methyl taurate sodium | — | — | — | — | — | — | 20 | — | — |
| Alkyl imidazoline | — | — | — | — | — | — | — | 20 | — |
| Isopropyl myristate | — | — | — | — | — | — | — | — | 10 |
| EDTA-3Na.2H$_2$O |  |  |  |  |  |  |  |  |  |
| Methyl parabane | 0.05 | 0.05 | 0.05 | 0.05 | 0.05 | 0.05 | 0.05 | 0.05 | 0.05 |
| Perfume | 0.1 | 0.1 | 0.1 | 0.1 | 0.1 | 0.1 | 0.1 | 0.1 | 0.1 |
| Purified water | 0.05* | 0.05* | 0.05* | 0.05* | 0.05* | 0.05* | 0.05* | 0.05* | 0.05* |
| Stability over time | x | x | ¤ | ¤ | ¤ | ¤ | ¤ | ¤ | X |
| Panel test results |  |  |  |  |  |  |  |  |  |
| Make-up removal effect | o | ▲ | ▲ | ▲ | ▲ | ▲ | x | x | o |
| Bare skin cleansing effect | x | o | ▲ | o | o | ▲ | ▲ | ▲ | ▲ |

*Balance to 100 wt %

In Table 2, Comparative Example 1 has a small mole number of added ethylene oxide (n=9.1), the skin cleansing agent thus obtained did not have good stability over time, and the bare skin cleansing effect was also not good.

Comparative example 4 has a large mole number of added ethylene oxide (n=18.2), and therefore the make-up removal effect is insufficient.

Comparative examples 2, 3, 5 and 6 use only a non-ionic surfactant(s) other than the polyethylene glycol fatty acid diesters, and thus the results were not satisfactory in terms of the make-up removal effect and the bare skin cleansing effect.

Comparative examples 7 and 8 do not contain a non-ionic surfactant(s), but contain an anion surfactant(s) or ampholytic surfactant(s), and therefore both the make-up removal effect and the bare skin cleansing effect were poor.

Comparative example 9 contains the polyethylene glycol fatty acid diester of this invention. However, it also contains liquid oil, and therefore the bare skin cleansing effect was poor and the stability standing over time was also not good.

EXAMPLE 8

| Dipropylene glycol | 5 (wt %) |
| Ethyl alcohol | 10 |
| EDTA-3Na.2H$_2$O | 0.05 |
| Carboxy vinyl polymer | 0.5 |
| Triethanolamine | 2 |
| PEG600 diisostearate | 20 |
| PEG400 monooleate | 5 |
| Methyl parabane | 0.1 |
| Perfume | Moderate amount |
| Purified water | Balance |

Preparation

The water soluble thickener was first dissolved in the main pot, and then the rest of the ingredients cited above, was dissolved one after another to obtain an agent of this invention. The skin cleansing agent thus obtained showed superior results both in terms of the make-up removal effect and the bare skin cleansing effect.

As describe thus far, the skin cleansing agent of this invention can perform, in a one-stage process, the removal of hard make-up and bare skin cleansing to the extent that sebum and dirt can be cleared out from the depth of pores, and it also has good stability over time.

What is claimed is:

1. An oil free skin cleansing agent comprising 1.0–80 wt % polyethylene glycol diisostearate having an added mole number of ethylene oxide of 10–18.

2. A skin cleansing agent according to claim 1, further comprising 30 wt % or less of polyethylene glycol monoisostearate having an added mole number of ethylene oxide of 4–14.

3. A skin cleansing agent according to claim 1 further comprising an additional 0.5–30 wt % polyoxyalkylene modified polysiloxane.

4. A skin cleansing agent according to claim 1, wherein the added mole number of ethylene oxide is 11–13.

5. A skin cleansing agent according to claim 1, wherein said polyethylene glycol diisostearate comprises 6–20% by weight.

6. A skin cleansing agent according to claim 3, wherein said polyoxyalkylene modified polysiloxane comprises 3–20% by weight.

7. A skin cleansing agent according to claim 3 wherein said polyoxyalkylene modified polysiloxane has a chemical formula of:

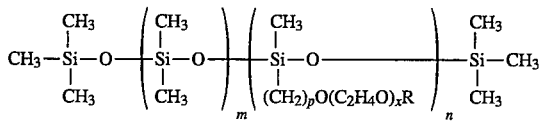

wherein, R is a hydrogen or an alkyl group with a carbon number of 1–5, p is an integer in the range of 1–5, x is an integer in the range of 5–30, and m and n are integers in the range of 1–15.

8. A skin cleansing agent according to claim 3 wherein said polyoxyalkylene modified polysiloxane is a co-polymer of dimethyl siloxane and methyl (polyoxyethylene) siloxane with an added amount of the ethylene oxide of 5–500 moles.

9. A skin cleansing agent according to claim 1 further comprising a water soluble compound with hydroxyl groups selected from the group consisting of ethyl alcohol, isopropyl alcohol, butanol, propylene glycol, isopropyl glycol, 1, 3 butanediol, dipropylene glycol, glycerine, polyglycerine, trimethylolpropane, erythritol, pentaerythritol, sorbitan, sorbitol glucose, mannitol, saccharose, trehalose, fructose, and their derivatives.

10. A skin cleansing agent according to claim 9 wherein said water soluble compound comprises 1–40 wt % of the total amount of the cleansing agent.

11. A skin cleansing agent according to claim 10 wherein said water soluble compound comprises 5–20 wt % of the total amount of the cleansing agent.

12. A skin cleansing agent according to claim 1, in a liquid, viscous or jelly form.

13. A skin cleansing agent according to claim 12, further comprising a water soluble thickener.

* * * * *